United States Patent

Mimura et al.

4,066,730

Jan. 3, 1978

[54] METHOD FOR PRODUCING REGENERATED CELLULOSE FIBERS HAVING EXCELLENT FLAMEPROOFNESS

[75] Inventors: Koji Mimura, Otake; Atsushi Kawai, Hiroshima; Yoshiya Kametani; Tetsuro Nakahama, both of Yokohama, all of Japan

[73] Assignee: Mitsubishi Rayon Co., Ltd., Tokyo, Japan

[21] Appl. No.: 661,859

[22] Filed: Feb. 27, 1976

[51] Int. Cl.² ............................................. D01F 2/08
[52] U.S. Cl. ........................... 264/191; 106/15 FP; 106/177; 260/45.7 P; 260/931; 264/197
[58] Field of Search ............ 260/931, 45.7 P; 106/15 FP, 177; 264/191, 194, 197

[56] References Cited

U.S. PATENT DOCUMENTS

| | | | |
|---|---|---|---|
| 3,058,941 | 10/1962 | Birum | 260/931 |
| 3,507,610 | 4/1970 | Tesoro et al. | 106/177 |
| 3,836,507 | 9/1974 | Yoshizawa et al. | 260/931 |

FOREIGN PATENT DOCUMENTS

| | | | |
|---|---|---|---|
| 961,443 | 6/1964 | United Kingdom | 260/931 |

*Primary Examiner*—Jay H. Woo

*Attorney, Agent, or Firm*—Oblon, Fisher, Spivak, McClelland & Maier

[57] ABSTRACT

Regenerated cellulose fibers having very good flameproofness are obtained by adding a polyphosphonate having the following formula:

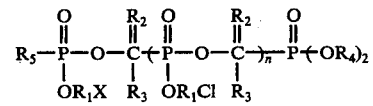

wherein $R_1$ is ethylene or propylene; $R_2$ and $R_3$ are methyl or ethyl which may be the same or different; $R_4$ is an alkyl group having 1 to 4 carbon atoms, or an aralkyl group in which the alkyl substituent has 1 to 4 carbon atoms and the hydrogen atoms in said alkyl and aralkyl groups may be substituted with chlorine or bromine; $R_5$ is an aromatic group having 1 to 20 carbon atoms or an unsaturated or saturated aliphatic or alicyclic group having 1 to 20 carbon atoms or a combination thereof and $R_5$ may contain carbonyl group, sulfonyl group or nitrogen; X is halogen, and n is an integer from 1 to 1000, to a viscose and then spinning the viscose by conventionally accepted procedures. The retention of the polyphosphonate flameproofing agent in the fibers can be markedly increased by this procedure.

11 Claims, No Drawings

METHOD FOR PRODUCING REGENERATED CELLULOSE FIBERS HAVING EXCELLENT FLAMEPROOFNESS

BACKGROUND OF THE INVENTION

1. Field of the Invention

The present invention relates to a method for producing regenerated cellulose fibers having excellent flameproofness.

2. Description of the Prior Art

Many methods have been proposed which impart flameproofness to regenerated cellulose fibers. The latest, well-known, commercial method is disclosed in U.S. Pat. No. 3,371,131 where a polyphosphonate which is represented by formula (2) and obtained by polymerizing a cyclic chlorophosphite and a ketone compound in an acidic medium

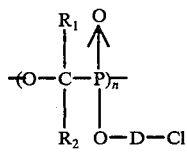

wherein D is an alkylene having 2 or 3 carbon atoms or an alkyl substituted alkylene in which the alkyl substituent has a total of not more than 8 carbon atoms and the alkylene has 2 or 3 carbon atoms; $R_1$ and $R_2$ are alkyl, phenyl, phenylalkyl, alkylphenyl, alkenyl or alkoxycarbonyl and $R_1$ and $R_2$ contain no more than 12 carbon atoms, and $n$ is an integer of 1 to 1000, is blended with a viscose to be spun. However, this method presents several problems. One of these problems is that the polyphosphonate represented by formula (2) is partially hydrolyzed with alkali in the viscose and has a tendency to shed into the coagulation bath in the spinning step which causes a substantial reduction in the amount of the polyphosphonate retained in the fiber. Another problem is that because the polyphosphonates hydrolyze during preparation of the viscose fibers, the waste water from the process contains low molecular weight phosphorous compounds and therefore presents a pollution problem. All of these troubles result from the characteristics of the polyphosphonates represented by formula (2).

That is, the phosphorus-containing polymers disclosed in U.S. Pat. No. 3,371,131 have an extremely broad molecular weight distribution for the reasons that no polymerization regulator (reaction-terminator) is used and that the polymerization velocity is relatively fast because the reaction is conducted in an acidic medium. For example, even those polyphosphonates having a mean molecular weight of 7000 include some extremely low molecular compounds. Furthermore, a cyclic phosphite structure or an active chloride remains at the molecular terminal of the phosphorus-containing polymers. Of course, conversion of trivalent phosphorous to pentavalent phosphorous occurs partially by the heat treatment during synthesis, but in any case, it is certain that the polymer terminals are in a very unstable state. The ability of such polyphosphonates to hydrolyze when treated with alkali bears a close relationship with the terminal structure of the polymer. Further, with a decrease in the molecular weight, which represents an increase in the number of terminals, or with an increase in the degree of instabiity of the polymer terminals, the polyphosphonates are more easily decomposed and so the retention of the polyphosphonate in the fibers is reduced. Still further, difficulties are apt to occur in the yarn spinning step. Therefore, in order to solve these troubles, it is important (1) to fix the terminals of the polymer and to adjust the degree of polymerization with a polymerization regulator and (2) to find the conditions under which good polymers of narrow molecular weight distribution (distribution of polymerization degree) are obtained by reducing the polymerization velocity as much as possible.

In view of the considerations above, detailed experimentation has led to the successful synthesis of polyphosphonate compounds having excellent hydrolysis resistance which is disclosed in a United States patent application filed concurrently herewith which is based on priority to Japanese patent application 46549/1975, filed Apr. 18, 1975.

SUMMARY OF THE INVENTION

Accordingly, one object of the present invention is to provide a method for producing regenerated cellulose fibers characterized by excellent flameproofness.

Briefly, this object and other objects of the present invention as hereinafter will become more readily apparent can be attained in a method of forming regenerated cellulose fibers having excellent flameproofness by adding a polyphosphonate represented by formula (1)

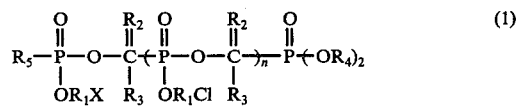

wherein $R_1$ is ethylene or propylene; $R_2$ and $R_3$ are methyl or ethyl which may be the same or different; $R_4$ is an alkyl group having 1 to 4 carbon atoms, or aralkyl in which the alkyl substituent has 1 to 4 carbon atoms and the hydrogen atoms in said alkyl and aralkyl groups may be substituted with chlorine or bromine; $R_5$ is an aromatic group having 1 to 20 carbon atoms or an unsaturated or saturated aliphatic or alicyclic group having 1 to 20 carbon atoms or a combination thereof and $R_5$ may contain carbonyl group, sulfonyl group or nitrogen; X is halogen, and $n$ is an integer from 1 to 1000, to a viscose in an amount of 5 to 40% by weight of the cellulose contained in the viscose; and then spinning the viscose in a coagulation bath.

DETAILED DESCRIPTION OF THE PREFERRED EMBODIMENTS

The present invention involves a method for producing regenerated cellulose fibers having excellent flameproofness by adding to a viscose a polyphosphonate represented by formula (1) in an amount of 5 to 40% by weight based on the cellulose content of the viscose,

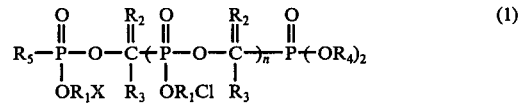

wherein $R_1$ is ethylene or propylene, $R_2$ and $R_3$ are methyl or ethyl which may be the same or different, $R_4$ is an alkyl group having 1 to 4 carbon atoms, or aralkyl group in which the alkyl substituent has from 1 to 4 carbon atoms and the hydrogen atoms in these groups may be substituted with chlorine or bromine, $R_5$ is an unsaturated or saturated aliphatic, alicyclic or aromatic compound group having 1 to 20 carbon atoms or combinations thereof and $R_5$ may contain carbonyl group, sulfonyl group or nitrogen, X is a halogen, and $n$ is an integer of from 1 to 1000. The two components are homogeneously mixed and the viscose is spun by a conventional method.

The polyphosphonates of formula (1) have excellent hydrolysis resistance and are obtained by fixing one terminal of the polyphosphonate while simultaneously regulating the polymerization degree of the polyphosphonate with the use of a triorganophosphite as a polymerization regulator. In addition, the other terminal of the polymer having a cyclic phosphite structure which remains unreacted, can then be reacted with an active halide to convert the trivalent phosphorous to pentavalent phosphorous and thereby fix this terminal of the polymer. Furthermore, in connection with the production of a polymer having a narrow molecular weight distribution, the active halide which effectively fixes one terminal of the polymer also functions as a polymerization catalyst. Consequently, it is not necessary to conduct the polymerization reaction in an acidic medium which constitutes an extremely severe reaction medium, and therefore, it is possible to conduct the polymerization under mild conditions. Therefore, the molecular weight distribution of the thus obtained polymer is extremely narrow and the polymer has excellent quality.

As previously explained, the polyphosphonate of formula (1) of the present invention can be obtained by reacting a cyclic chlorophosphite represented by formula (3), a ketone compound represented by formula (4), a triorganophosphite compound represented by formula (5), and an active halide represented by formula (6), all of which have been sufficiently purified, under a nitrogen atmosphere at $-50°$ to $200°$ C, preferably $0°$ to $100°$ C.

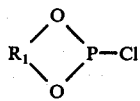
(3)

$R_1$ in the formula has previously been defined. Suitable compounds represented by formula (3) include ethylene chlorophosphite, propylene chlorophosphite, and the like.

Suitable compounds represented by formula (4) below include acetone, methyl ethyl ketone, diethyl ketone, and the like,

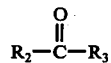
(4)

wherein $R_2$ and $R_3$ are as defined previously.

Suitable compounds represented by formula (5) below include trimethyl phosphite, triethyl phosphite, tripropyl phosphite, tributyl phosphite, dimethyl ethyl phosphite, triisopropyl phosphite, tris-2-chloroethyl phosphite, tris-2-bromoethyl phosphite, tris-2,3-dibromopropyl phosphite, tris-2,3-chlorobromopropyl phosphite, and the like, $P(OR_4)_3$ (5)

wherein $R_4$ is as previously defined.

Suitable compounds represented by formula (6) below include halogenated hydrocarbons such as methyl iodide, ethyl chloride, n-propyl chloride, isopropyl bromide, n-butyl chloride, iso-butyl chloride, tert-butyl chloride, allyl chloride, methallyl chloride, cyclohexyl chloride, benzyl chloride, dibenzyl chloride, phenethyl chloride, chloromethyl styrene, and the like; acid halides such as acetyl chloride, benzoyl chloride, phthaloyl chloride, and the like; sulfonyl halides such as benzenesulfonyl chloride, p-toluenesulfonyl chloride, and the like; and N-halides such as cyanuric chloride, N-chlorosuccinimide, N-bromosuccinimide, 1,3-dichlorohydantoin, 1,3-dichloro-5,5'-dimethylhydantoin, trichloroisocyanuric acid, and the like, $R_5-X$ (6)

wherein $R_5$ is as previously defined.

In the preparation of a polyphosphonate it is preferred to conduct the reaction under mild conditions using inactive solvents such as ethane dichloride, methylene chloride, trichlene (trichloroethylene), methylchloroform, carbon tetrachloride, ethylene tetrachloride, trichloroethane, acetonitrile, tetrahydrofuran, dioxane, chloroform, benzene, toluene, xylene, monochlorobenzene, o-dichlorobenzene, and the like. These inactive solvents are sufficiently purified before use. Both the reactants and the solvents are sufficiently purified because if the catalytic effect of the active halide of formula (6) is to be effectively attained, it is important to avoid an acidic medium for the reaction system. Such undesirable acidic media will be formed by the presence of only very slight amounts of water, which may be present in the solvent and reactants. Polymerization of the reactants in an acidic medium results in too high a polymerization velocity and a very broad molecular weight distribution of the polyphosphonate product.

As explained above, the polyphosphonate of formula (1) used in the present invention is very similar to the conventional polyphosphonate of formula (2) in its structural formula. This similarity in structure is not carried over to similarity in properties because the properties of the present polyphosphonates are completely different from the properties of the conventional polymer.

The method for producing regenerated cellulose fibers using the polyphosphonate of formula (1) is explained below. The addition of the polyphosphonate of formula (1) to a viscose and the subsequent mixture of the components may be conducted by the conventional methods. However, in general, the polyphosphonate is dissolved in a suitable organic solvent, for example, a chlorinated solvent such as methylene chloride, chloroform, carbon tetrachloride, methylchloroform, dichloroethane, trichlene, perchlene (tetrachloroethylene), or the like; an aromatic hydrocarbon such as benzene, toluene, xylene, or the like; an ester such as ethyl acetate, butyl acetate, or the like; an alcohol such as propanol, butanol, or the like; a nitrile compound such as acetonitrile, or the like; or low molecular weight organic liquid phosphorous compounds, or the like, and the resultant solution is added to a viscose. Alternatively, the polyphosphonate may be emulsified with a suitable emulsifier and then the emulsion is added to a viscose. Still further, these two methods may be combined. It is a matter of course that other phosphorous compounds or other flameproofing agents may be used in combination with the polyphosphonate of the present invention.

The amount of the polyphosphonate of formula (1) which is added to the viscose may vary depending on the degree of flameproofness desired. Generally, it can be added in an amount of 5 to 40% by weight of the cellulose in the viscose.

The conditions under which the viscose fiber is spun are not critical and any of the known methods may be employed. One such example of a preferred conventional method employs a viscose having a cellulose concentration of 4 to 10% by weight, an alkali concentration of 3 to 8% by weight, a salt point of 5 to 20, and a viscosity of 40 to 500 poises (20° C); a coagulation bath containing 10 to 120 g/l of sulfuric acid, 20 to 350 g/l of sodium sulfate, and 0 to 150 g/l of zinc sulfate; and a temperature of 10° to 70° C for the coagulation bath.

However, spinning conditions which are especially preferred in order to attain the objects of the present invention are as follows:

| Viscose: | |
|---|---|
| Cellulose concentration | 5 to 8% by weight |
| Alkali concentration | 3 to 5% by weight |
| Viscosity | 100 to 400 poises |
| Salt point | 12 to 20 |
| Coagulation bath: | |
| Sulfuric acid | 10 to 30 g/l |
| Sodium sulfate | 20 to 100 g/l |
| Zinc sulfate | 0.1 to 0.6 g/l |
| Temperature | 10° to 30° C |

Stretching and regeneration:
1. Filaments can be stretched by 30 to 150%, preferably 60 to 110% in a second bath containing 0 to 30 g/l (more preferably 0.5 to 15 g/l) of sulfuric acid at 70° to 100° C. Therafter, regeneration is completed.
2. Alternatively, filaments can be stretched 30 to 150%, preferably 60 to 110% in air, and then they are passed through a bath containing not more than 1.5 g/l, preferably 0.5 to 15 g/l of sulfuric acid at 50° to 100° C, preferably 70° to 100° C, while maintaining their length. Regeneration is then completed.

When spinning and stretching of the fibers are conducted under the above conditions, the flameproofing agent is homogeneously dispersed in the fibers, the yarn spinning properties are excellent, and the properties of the fibers obtained are also good. An additional advantage is that stability of the spinning and stretching operation is very substantial.

As explained above, fibers having excellent flameproofness can be obtained by adding the polyphosphonate of the formula (1) to a viscose and then spinning the viscose under the conditions described. Furthermore, since the hydrolysis resistance of the polyphosphonate is substantially improved in the present invention, the retention of the polyphosphonate in the fibers during spinning is noticeably increased which results in improved economy.

Having generally described this invention, a further understanding can be obtained by reference to certain specific examples which are provided herein for purposes of illustration only and are not intended to be limiting unless otherwise specified. In the Examples, parts and percentages are given by weight, except for the stretching ratios.

EXAMPLE 1

A 1 liter separatory flask provided with a stirrer, a thermometer, a reflux condenser, a dropping funnel, and a nitrogen flow inlet device was charged with 253 parts of purified ethylene chlorophosphite, 386 parts of purified methylchloroform, and 15.5 parts of purified tris-2-chloropropyl phosphite. Then, a dropping funnel was charged with 116 parts of purified acetone and 1.9 parts of purified tert-butyl chloride.

While under a sufficient flow of dried nitrogen gas, the outside of the flask was cooled in an ice-water bath and the mixed solution of acetone and tert-butyl chloride was dropped with stirring into the flask during which addition the temperature within the flask was kept at 5° to 10° C. After addition of the reagent was completed, the reactants were allowed to stand at room temperature for about 48 hours. The polymer obtained existed as 384.9 parts of a solid portion and had the following structure:

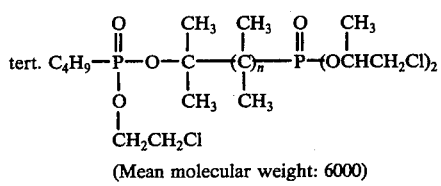

(Mean molecular weight: 6000)

EXAMPLE 2

A viscose which was prepared by adding 48% based on the weight of cellulose of carbon disulfide to alkali cellulose and which had a cellulose concentration of 7.5% and an alkali concentration of 4.2% was ripened until the viscosity reached 200 poises and the salt point reached 16. To 100 parts of the prepared viscose was added 3.5 parts of a solution of the polyphosphonate prepared in Example 1 in methylchloroform. The solution was mixed to homogeneity. Thereafter, the viscose was spun into a coagulation bath containing 18 g/l of sulfuric acid, 70 g/l of sodium sulfate, and 0.4 g/l of zinc sulfate at 30° C. The filaments withdrawn from the coagulation bath were stretched by 100% in a second bath containing 2 g/l of sulfuric acid at 80° C and were successively treated in a third bath containing 5 g/l of sulfuric acid at 60° C to complete regeneration. Thereafter, the filaments were subjected to the conventional after-treatments such as desulfurization, bleaching, acid treatment, lubrication, and drying.

In the present Example, essentially no sticky materials were recognized as forming during the spinning step which is a problem when conventional polyphosphonates are used.

Moreover, in the present Example, the retention of the polyphosphonate (flameproofing agent) in the fibers was 95.5% which is extremely high. Furthermore, there were no troubles in the yarn spinning operation of the obtained fibers and the limit of the oxygen index (L.O.I.) of the fibers was 27.5 which indicates that the fibers had excellent flameproofness.

EXAMPLE 3

In essentially the same method as described in Example 1, polyphosphonates were prepared using various reactants as shown in the following Table.

Each of the obtained polyphosphonates was added to a viscose and the viscose was spun under the same conditions as described in Example 2. The spinning state and the flameproofness of the fibers obtained are also shown in the Table.

bers was 80% which is a level substantially less than the levels achieved by the present process.

Having now fully described the invention, it will be

| Preparation of the flameproofing agent Reagents | (Parts) | Solution of flameproofing agent | | | Spinning | | | Spinning of fibers into yarn | Flameproofness (L.O.I) |
|---|---|---|---|---|---|---|---|---|---|
| | | Concentration (%) | Viscosity (poise) | Molecular weight[2] | Addition amount (% per cellulose)[3] | Retention (%) | Sticky materials | | |
| Propylenechlorophosphite | 281 | | | | | | Substantially no sticky materials were formed | | |
| Acetone | 116 | | | | | | | | |
| Tris-2-chloroethyl phosphite | 14 | 50.3 | 1.7 | 4500 | 28 | 94.9 | | Good | 27.5 |
| Benzoyl chloride | 2.8 | | | | | | | | |
| Dichloroethane (solvent) | 410 | | | | | | | | |
| Propylenechlorophosphite | 281 | | | | | | | | |
| Acetone | 116 | | | | | | | | |
| Tris-2-chloropropyl phosphite | 9.3 | 49.1 | 6.4 | 11200 | 25 | 97.4 | " | " | 27.0 |
| Benzenesulfonyl chloride | 3.5 | | | | | | | | |
| Carbon tetrachloride (solvent) | 436 | | | | | | | | |
| Ethylenechlorophosphite | 253 | | | | | | | | |
| Methylethylketone | 144 | | | | | | | | |
| Tris-2-chloroethylphosphite | 16.8 | 49.5 | 2.3 | 4900 | 20 | 95.7 | " | " | 26.0 |
| Allylchloride | 1.5 | | | | | | | | |
| Dichloromethane (solvent) | 415 | | | | | | | | |

(1) The reagents were all purified before use.
(2) Molecular weight of the flameproofing agent.
(3) The amount of flameproofing agent added.

EXAMPLE 4

A viscose having a cellulose concentration of 8.0% and an alkali concentration of 6.0% was ripened until it had a viscosity of 47 poises and a salt point of 7.1. A mixture of 50 parts of flameproofing agent solution 3 in Example 3 and 4 parts of tris-(chloroethyl)phosphate, per 100 parts of cellulose in the viscose, was added to the viscose and the mixture was homogeneously mixed. Thereafter, the viscose was spun into a coagulation bath containing 90 g/l of sulfuric acid, 15 g/l of zinc sulfate, and 350 g/l of sodium sulfate at 45° C. The filaments thus formed were stretched by 45% in a second bath containing 5 g/l of sulfuric acid at 80° C and were treated in a bath containing 5 g/l of sulfuric acid at 60° C to complete the regeneration. In accordance with the conventional procedure, the filaments were successively subjected to desulfurization, bleaching, acid treatment, lubrication, and drying.

Spinning of the filaments was conducted continuously for a long period of time, but substantially no formation of sticky materials was recognized and the spinning could be stably effected. Therefore, no difficulty was encountered in the yarn spinning of the fibers. The L.O.I. of the fibers was 27 which indicates that the fibers had excellent flameproofness.

Comparative Example

The same apparatus described in Example 1 was used. The flask was charged with 281 parts of purified propylene chlorophosphite and 410 parts of purified dichloroethane. The dropping funnel was charged with 116 parts of purified acetone and 0.4 part of water. The acetone solution was added to the flask under the same conditions as described in Example 1 to effect polymerization. The polyphosphonate obtained had a mean molecular weight of 15,000 and the molecular weight distribution was very broad. A 50% solution of the polyphosphonate in dichloroethane was added to a viscose under the same conditions described in Example 2 and the viscose was spun under the same conditions described in Example 2. In the present Comparative Example, the retention of the polyphosphonate in the fiapparent to one of ordinary skill in the art that many changes and modifications can be made thereto without departing from the spirit or scope of the invention as set forth herein.

What is claimed as new and intended to be covered by Letters Patent is:

1. A method for producing regenerated cellulose fibers having excellent flameproofness, which comprises:

adding a polyphosphonate represented by formula (1)

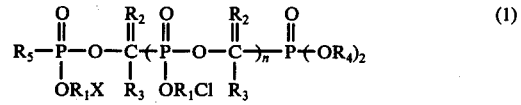

(1)

wherein $R_1$ is ethylene or propylene; $R_2$ and $R_3$ are methyl or ethyl which may be the same or different; $R_4$ is an alkyl group having 1 to 4 carbon atoms, or an aralkyl group in which the alkyl substituent has 1 to 4 carbon atoms and the hydrogen atoms in said alkyl and aralkyl groups may be substituted with chlorine or bromine; $R_5$ is an unsaturated or saturated aliphatic, alicyclic or aromatic group having 1 to 20 carbon atoms or combinations of said groups defining $R_5$ and $R_5$ may be a carbonyl group, or sulfonyl group containing substituent; X is halogen, and n is an integer from 1 to 1000, to a viscose in an amount of 5 to 40% by weight of the cellulose contained in the viscose; and then spinning the viscose in a coagulation bath.

2. The method of claim 1, wherein said polyphosphonate is dissolved in a viscose containing 4 to 10% by weight of cellulose and 3 to 8% by weight of an alkali, and having a salt point of 5 to 20 and a viscosity of 40 to 500 poises.

3. The method of claim 2, wherein said polyphosphonate is dissolved in a viscose containing 5 to 8% by weight of cellulose and 3 to 5% by weight of alkali, and having a salt point of 12 to 20 and a viscosity of 100 to 400 poises.

4. The method of claim 1, wherein said viscose is spun into a coagulation bath containing 10 to 120 g/l of sulfuric acid, 20 to 350 g/l of sodium sulfate, and 0 to 150 g/l of zinc sulfate at 10° to 70° C.

5. The method of claim 4, wherein the viscose is spun into a coagulation bath containing 10 to 30 g/l of sulfuric acid, 20 to 100 g/l of sodium sulfate, and 0.1 to 0.6 g/l of zinc sulfate at 10° to 30° C.

6. The method of claim 1, wherein tris-2-chloroethyl phosphite is additionally dissolved in said viscose.

7. The method of claim 1, wherein said polyphosphonate is dissolved in a solvent selected from the group consisting of methylchloroform, dichloroethane, and carbon tetrachloride and the solution obtained is added to said viscose.

8. The method of claim 1, wherein filaments withdrawn from said coagulation bath are stretched by 30 to 150% in a second bath containing 0 to 30 g/l of sulfuric acid at 70° to 100° C.

9. The method of claim 8, wherein said filaments withdrawn from said coagulation bath are stretched by 60 to 110% in a second bath containing 0.5 to 15 g/l of sulfuric acid.

10. The method of claim 1, wherein filaments withdrawn from said coagulation bath are stretched by 30 to 150% in air and then treated in an aqueous bath containing not more than 15 g/l of sulfuric acid at 50° to 100° C while maintaining the filaments at the lengths to which they were stretched.

11. The method of claim 10, wherein said filaments withdrawn from said coagulation are stretched by 60 to 110% in air and then treated in an aqueous bath containing 0.5 to 15 g/l of sulfuric acid at 70° to 100° C while maintaining the filaments at the lengths to which they were stretched.

* * * * *

UNITED STATES PATENT AND TRADEMARK OFFICE
CERTIFICATE OF CORRECTION

PATENT NO. : 4,066,730
DATED : January 31, 1978
INVENTOR(S) : Mimura et al

It is certified that error appears in the above-identified patent and that said Letters Patent are hereby corrected as shown below:

Please insert the following information:

--[30] Foreign Application Priority Data:

April 18, 1975  Japan.................50-46549
April 18, 1975  Japan.................50-47925--

Signed and Sealed this

Thirteenth Day of June 1978

[SEAL]

Attest:

RUTH C. MASON
Attesting Officer

DONALD W. BANNER
Commissioner of Patents and Trademarks